(12) United States Patent
Apdalhaliem et al.

(10) Patent No.: US 10,983,078 B2
(45) Date of Patent: Apr. 20, 2021

(54) METHODS AND SYSTEMS FOR DESIGNING A COMPOSITE STRUCTURE

(71) Applicant: The Boeing Company, Chicago, IL (US)

(72) Inventors: Sahrudine Apdalhaliem, Seattle, WA (US); Heh-Chyun Cliff Chen, Bellevue, WA (US); Waeil M. Ashmawi, Bellevue, WA (US); Kimberly D. Meredith, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/691,896

(22) Filed: Nov. 22, 2019

(65) Prior Publication Data
US 2020/0088661 A1   Mar. 19, 2020

Related U.S. Application Data

(63) Continuation of application No. 14/745,813, filed on Jun. 22, 2015, now abandoned.

(51) Int. Cl.
*G01N 25/00* (2006.01)
*G01N 17/00* (2006.01)
(Continued)

(52) U.S. Cl.
CPC .............. *G01N 25/00* (2013.01); *B64F 5/60* (2017.01); *G01N 17/00* (2013.01); *G01N 33/442* (2013.01); *G01N 5/025* (2013.01)

(58) Field of Classification Search
CPC .... G01N 27/048; G01N 33/383; G01N 25/00; G01N 17/00; G01N 5/025; B64F 5/60
(Continued)

(56) References Cited

U.S. PATENT DOCUMENTS 3,283,561 A * 11/1966 Fricke ................. G01N 23/12
                                                          374/15
4,701,052 A * 10/1987 Schoen, Jr. ........... G01N 25/68
                                                         356/369
(Continued)

FOREIGN PATENT DOCUMENTS

CN       103208047 A     7/2013
CN       103419922 A    12/2013
(Continued)

OTHER PUBLICATIONS

Unnam, J. et al: "Analytical Prediction of Moisture Absorption/Desorption in Resin Matrix Composites Exposed to Aircraft Environments", 18th Structural Dynamics and Materials Conference, Mar. 21, 1977-Mar. 23, 1977, vol. 77-400, pp. 227-235.
(Continued)

*Primary Examiner* — Gail Kaplan Verbitsky
(74) *Attorney, Agent, or Firm* — Armstrong Teasdale LLP

(57) ABSTRACT

A computer-implemented method of determining moisture content of a composite structure is provided. The method includes performing a thermal analysis calculation on the composite structure to determine a temporal surface temperature profile of the composite structure based on temporal environmental parameter profiles, wherein the surface temperature profile is determined independently of a moisture content of the composite structure. The method also includes performing a moisture content analysis calculation on the composite structure to determine a moisture content of the composite structure, wherein the moisture content analysis calculation is based on the determined temporal surface temperature profile and a thickness of the composite structure. The thermal analysis calculation is performed iteratively with a first time period and the moisture content
(Continued)

analysis calculation is performed iteratively with a second time period that is longer than the first time period.

15 Claims, 5 Drawing Sheets

(51) Int. Cl.
    *G01N 33/44*     (2006.01)
    *B64F 5/60*     (2017.01)
    *G01N 5/02*     (2006.01)

(58) Field of Classification Search
    USPC .......................................................... 73/73
    See application file for complete search history.

(56) References Cited

U.S. PATENT DOCUMENTS

| | | | |
|---|---|---|---|
| 6,030,673 A * | 2/2000 | Andersen | B32B 5/14 |
| | | | 428/36.4 |
| 6,393,726 B1 | 5/2002 | Momose et al. | |
| 6,690,016 B1 * | 2/2004 | Watkins | G01N 25/72 |
| | | | 250/341.7 |
| 7,237,946 B2 * | 7/2007 | Lindstrom | G01N 25/66 |
| | | | 374/16 |
| 7,778,786 B2 * | 8/2010 | Ding | B07C 5/14 |
| | | | 162/260 |
| 7,807,971 B2 | 10/2010 | Grace et al. | |
| 8,032,244 B2 * | 10/2011 | Trost | G01N 33/383 |
| | | | 204/426 |
| 8,692,201 B1 | 4/2014 | Gordon, III et al. | |
| 8,732,977 B2 | 5/2014 | Adams et al. | |
| 8,855,803 B2 * | 10/2014 | Ciuperca | B29C 39/00 |
| | | | 700/198 |
| 9,381,730 B2 * | 7/2016 | Evens | B29C 73/163 |
| 10,272,920 B2 * | 4/2019 | Shikii | B60W 40/08 |
| 2006/0274812 A1 | 12/2006 | Safai et al. | |
| 2008/0046209 A1 * | 2/2008 | Ding | B07C 5/14 |
| | | | 702/81 |
| 2008/0154518 A1 * | 6/2008 | Manaka | G01F 1/684 |
| | | | 702/24 |
| 2011/0132523 A1 | 6/2011 | Evens et al. | |
| 2011/0188535 A1 * | 8/2011 | Boehm | G01N 25/68 |
| | | | 374/20 |
| 2013/0306220 A1 * | 11/2013 | Graham | B29C 73/10 |
| | | | 156/73.6 |
| 2014/0000788 A1 * | 1/2014 | Evens | B29C 73/12 |
| | | | 156/94 |
| 2014/0220277 A1 * | 8/2014 | Lewis | F16L 59/021 |
| | | | 428/36.4 |
| 2014/0283595 A1 * | 9/2014 | Huang | G01F 1/699 |
| | | | 73/204.17 |
| 2017/0219553 A1 * | 8/2017 | Radjy | G01N 33/383 |
| 2018/0238820 A1 * | 8/2018 | Ghods | G01N 27/026 |

FOREIGN PATENT DOCUMENTS

| | | | |
|---|---|---|---|
| CN | 103665416 A | | 3/2014 |
| CN | 104493081 A | | 4/2015 |
| JP | S60210749 A | | 10/1985 |
| JP | H02114161 A | | 4/1990 |
| JP | H06118040 A | | 4/1994 |
| JP | 02001228264 A | * | 8/2001 |
| JP | 2009516161 A | | 4/2009 |
| WO | 03097345 A1 | | 11/2003 |
| WO | 2014057429 A1 | | 2/2014 |
| WO | 2014108695 A1 | | 7/2014 |

OTHER PUBLICATIONS

Vodicka, Roger: "Accelerated Enviromental Testing of Composite Materials", Apr. 1998 (Apr. 1998), Melbourne, AU, pp. 13-14, 38.
Seneviratne, Waruna P. et al: "Environmental Compensation Factor Influence on Composite Design and Certification", FAA JAMS 2012 Technical Review Meeting, Apr. 5, 2012 (Apr. 5, 2012), Baltimore, USA, pp. 12-13.
EP Examination Search Report for related Application No. 16170785.6-1559, dated Jul. 27, 2016, 4 pages.
Exteneded European Search Report for related Application No. 16170785.6-1559, dated Oct. 21, 2016, 8 pages.
EP Intention to Grant for related Application No. 16170785.6-1559, dated Apr. 2, 2019, 5 pp.
Japanese Office Action regarding Japanese Patent Application No. 2016-119652 dated Apr. 28, 2020.
China First Office Action, Application No. 201610452933.3, dated Jul. 30, 2020, 9 pps.: with English translation.

* cited by examiner

METHODS AND SYSTEMS FOR DESIGNING A COMPOSITE STRUCTURE

CROSS-REFERENCE TO RELATED APPLICATION

This application is a continuation and claims priority to U.S. patent application Ser. No. 14/745,813 filed Jun. 22, 2015 for METHODS AND SYSTEMS FOR DETERMINING AN ALLOWABLE MOISTURE CONTENT IN A COMPOSITE STRUCTURE, which is hereby incorporated by reference in its entirety.

BACKGROUND

The present application relates to a method of determining an allowable moisture content of a structure, and, more particularly, to a method of determining an allowable moisture content of composite structure used in the manufacture of aircraft.

Non-metallic structures have many advantages over their metallic counterparts. Most notably, they provide significant weight savings without a corresponding loss of strength, for example through the accurate alignment of non-metallic fibers to the direction of the expected applied load. The fibers are arranged in a number of overlapping layers, or plies.

Certain groups of materials, such as certain plastics and epoxy resin composite structures, readily absorb moisture by diffusion. Whilst this is a relatively slow process (the amount of absorption is measured in terms of millimeters over time periods measured in weeks, months and years), the presence of moisture within a material may shorten the useful service lifetime of the material. Additionally, prolonged exposure to relatively high temperatures may also shorten the useful service lifetime of the material. It is therefore necessary to take into account the effects of high temperature and moisture content during the design process.

Conventionally, a constant saturation level has been used in the design of composite materials independent of the size and scale of the composite structure. The constant saturation level is measured as a moisture percentage weight of the dry composite structure. For example, the maximum allowable moisture content (saturation level) is attained when the weight of the moisture content within the structure reaches a predetermined percentage weight of the composite structure with zero moisture. The conventional saturation level was designed for relatively thin composite structures having between about 30-40 plies. However, modern composite structures may include as many as 50-100 plies. Modern composite structures having increased thickness are able to absorb proportionately more moisture without affecting the service lifetime of the component. As such, the traditional predetermined saturation level results in over-engineered composite structures that increase the weight of the aircraft and increase manufacturing time and costs.

Furthermore, the calculations performed to determine the saturation level include performing a thermal analysis and a moisture diffusion analysis as a coupling. Such calculations include vast amounts of data and require a significant amount of computing power and time to determine.

Accordingly, there is a need for a method of determining a moisture saturation level for relatively thick composite structures that requires less time and computing power.

BRIEF DESCRIPTION

In one aspect, a computer-implemented method of determining moisture content of a composite structure is provided. The method includes performing a thermal analysis calculation on the composite structure to determine a temporal surface temperature profile of the composite structure based on temporal environmental parameter profiles, wherein the surface temperature profile is determined independently of a moisture content of the composite structure. The method also includes performing a moisture content analysis calculation on the composite structure to determine a moisture content of the composite structure, wherein the moisture content analysis calculation is based on the determined temporal surface temperature profile and a thickness of the composite structure. The thermal analysis calculation is performed iteratively with a first time period and the moisture content analysis calculation is performed iteratively with a second time period that is longer than the first time period.

In another aspect, moisture content determination system is provided. The system includes an environmental parameter database including environmental parameter data related to a plurality of environmental parameters from a plurality of airports, and a parameter profile module configured to generate a plurality of temporal environmental parameter profiles based on the environmental parameter data, wherein each parameter environmental profile is based on an environmental parameter of the plurality of environmental parameters. A surface temperature module is configured to perform a thermal analysis calculation to generate a temporal surface temperature profile of the composite structure for the plurality of airports, wherein the surface temperature module generates the temporal surface temperature profile based on the generated temporal environmental parameter profiles, and wherein the surface temperature profile is generated independently of a moisture content of the composite structure. A moisture content module is configured to perform a moisture content analysis calculation to determine a moisture content of the composite structure based on the generated temporal surface temperature profile and a thickness of the composite structure, wherein the thermal analysis calculation is performed iteratively with a first time period and the moisture content analysis calculation is performed iteratively with a second time period that is longer than the first time period.

In yet another aspect, at least one non-transitory computer-readable storage media is provided. The media has computer-executable instructions embodied thereon, wherein when executed by at least one processor, the computer-executable instructions cause the at least one processor to perform, using a surface temperature module, a thermal analysis calculation on a composite structure to determine a temporal surface temperature profile of the composite structure based on temporal environmental parameter profiles, wherein the surface temperature profile is determined independently of a moisture content of the composite structure. The instructions also cause the processor to perform, using an allowable moisture content module, a moisture content analysis calculation on the composite structure to determine a moisture content of the composite structure, wherein the moisture content analysis calculation is based on the determined temporal surface temperature profile and a thickness of the composite structure, wherein the thermal analysis calculation is performed iteratively with a first time period and the moisture content analysis calculation is performed iteratively with a second time period that is longer than the first time period.

DETAILED DESCRIPTION

Figure 1:
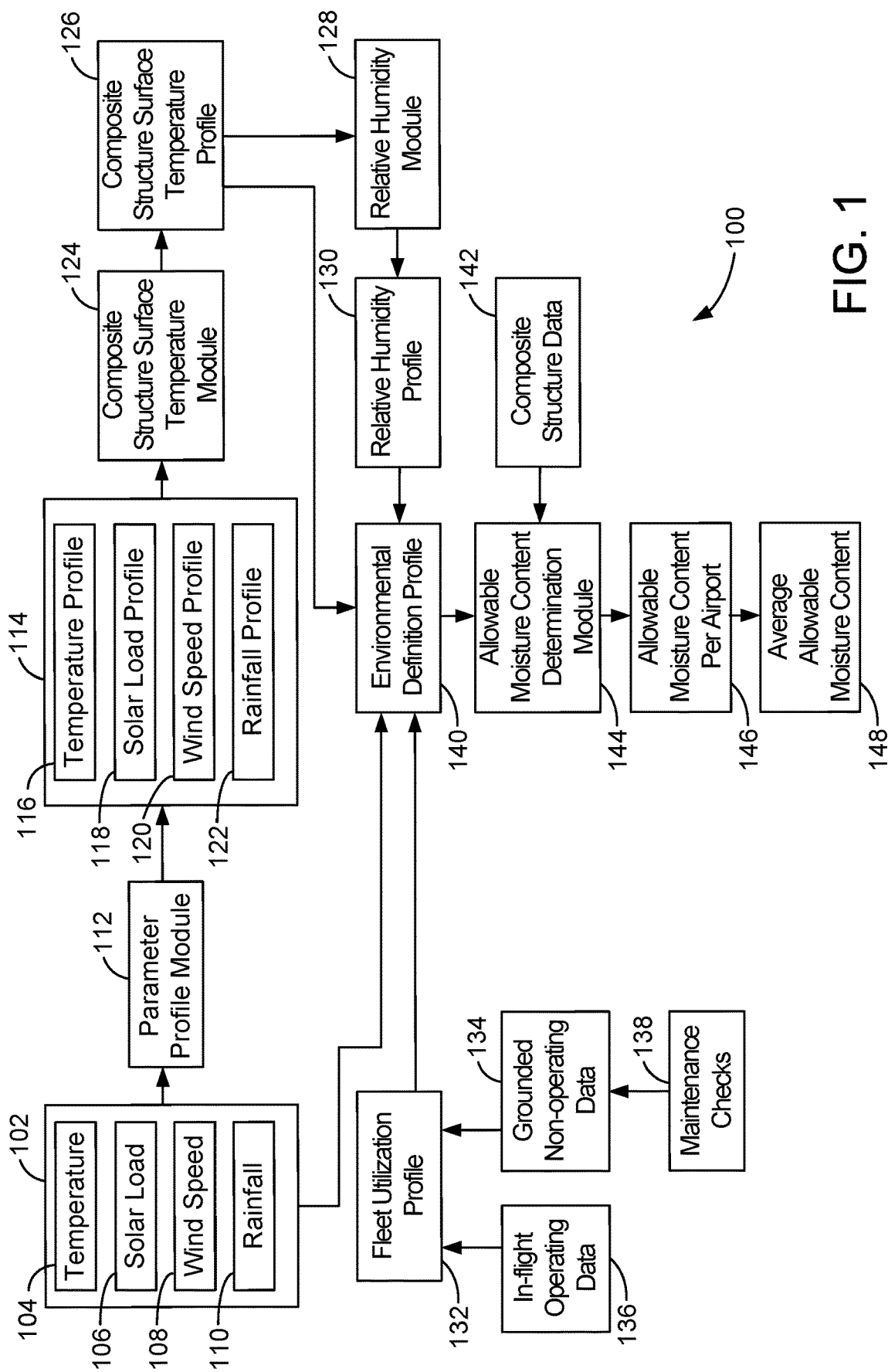
FIG. 1 illustrates an exemplary flow diagram for implementing an exemplary allowable moisture content determination system.

Currently, composite structures are designed on the basis that a composite structure saturated to its allowable moisture content has a strength that is less than the theoretical strength of the composite structure when completely unsaturated. As described herein, for larger structures, for example a commercial aircraft, it is not unknown for the composite components to have thicknesses on the order of 50 mm. Composite structures of this order of magnitude are extremely unlikely to become saturated throughout their full thickness over the course of their service lifetime. As such, it is desired to determine an allowable moisture content of the composite structure based on its thickness. As disclosed herein, composite structures are manufactured according to the newly calculated moisture intake based on its thickness such that thinner gauge composite structures are produced that maintain a required amount of strength, but reduce the overall weight of the aircraft and may reduce the manufacturing costs associated therewith.

In one implementation, a computer program is provided, and the program is embodied on a computer-readable medium. In an example implementation, the computer program is executed on a single computing device, without requiring a connection to a server computer. The computer program is flexible and designed to run in various different environments without compromising any major functionality. In some implementations, the system includes multiple components distributed among a plurality of computing devices. One or more components may be in the form of computer-executable instructions embodied in a computer-readable medium. The systems and processes are not limited to the specific implementations described herein. In addition, components of each system and each process can be practiced independent and separate from other components and processes described herein. Each component and process can also be used in combination with other assembly packages and processes.

The term "moisture content", as used herein, generally refers to the amount of water in a material, for example a hygroexpansive, composite material, and the amount can be expressed in any units known to one of skill in the art. In some embodiments, the units can be expressed in percent by weight, for example, and can refer to the percent water based on the weight of the sample in its water free state.

The term "hygroexpansive material" can refer to a material that experiences a change in volume with a change in moisture content. The term "hygroexpansive composite material" refers to a material that can absorb moisture, can expand as it takes up water, and is composed of more than one component. In some embodiments, the material comprises a hygroscopic component. One of skill will appreciate that a composite material can take several forms. In some embodiments, for example, the terms "composite material" and "composite structure" can be used interchangeably. Synthetic materials fabricated from multiple components, each having the same or different compositions, are another example. Such materials can include woven and non-woven materials having a composite of numerous fibrous elements that have the same or different individual compositions.

The hygroexpansive composite materials described herein include resin composite materials for use in aircraft, e.g., aircraft skin. The resin composite materials described herein include fiber reinforced composite materials. The resins include epoxy resins, and the reinforcing fibers include carbon fibers. In other preferred embodiments, the resins of the composite materials may include polyimide resins, bismaleimide resins and phenol resins, and the reinforcing resins may include glass fibers, ceramic fibers and alamide fibers. Generally, the composite materials or composite structures described herein may be any type of composite materials used in any application benefiting from the use of composite materials.

As used herein, an element or step recited in the singular and preceded with the word "a" or "an" should be understood as not excluding plural elements or steps, unless such exclusion is explicitly recited. Furthermore, references to "example implementation" or "one implementation" of the present disclosure are not intended to be interpreted as excluding the existence of additional implementations that also incorporate the recited features.

FIG. 1 illustrates an exemplary flow diagram for implementing an exemplary allowable moisture content determination system 100. In the exemplary implementation, system 100 includes an environmental parameter database 102 that stores data related to a plurality of various environmental parameters that may be used to determine an allowable moisture content for a composite structure, as described in further detail below. Specifically, environmental parameter database 102 stores at least temperature data 104, solar load data 106, wind speed data 108, and rainfall data 110. In the exemplary implementation, database 102 stores the environmental parameter data for a plurality of airports. More specifically, database 102 stores the environmental parameter data for at least 12 airports having the determined highest moisture intake. Airports having the highest determined moisture intake are used such that the final allowable moisture content determination is a conservative estimate, while still providing for a more accurate determination of allowable moisture content for thicker magnitude composite structures. Database 102 includes environmental parameter data collected at an hourly rate over a period of 40 years.

System 100 also includes a parameter profile module 112 that determines a plurality of parameter profiles 114 based on the environmental parameter data from database 102. More specifically, module 112 determines a parameter profile 114 for each of the different environmental parameters for which data is stored in database 102. For example, module 112 generates a temperature profile 116 from temperature data 104, a solar load profile 118 from solar load data 106, a wind speed profile 120 from wind speed data 108, and a rainfall profile 122 from rainfall data 110. Module 112 is not limited to only generating the profiles described above, but may generate a profile from data for any environmental parameter stored in database 102. In the exemplary implementation, each parameter profile 114 is generated from environmental parameter data from one of the parameters in database 102. That is, environmental parameter data from each airport of the plurality of airports is used to generate a parameter profile 114 for each environmental parameter.

Allowable moisture content determination system 100 also includes a composite structure surface temperature module 124 that is configured to perform at least a portion of a thermal analysis to generate an estimated surface temperature profile 126 of a composite structure for the plurality of airports. In the exemplary implementation, surface temperature profile 126 is based on parameter profiles 114 that include the environmental parameter data and is generated independently of a moisture content or moisture analysis of a composite structure. More specifically, module 124 calculates an average surface temperature of a composite structure via an interpolation method over a predetermined time period based on environmental parameter profiles 114.

The surface temperature of a composite structure is one parameter that determines an overall moisture intake. Specifically, the higher the surface temperature of a composite structure, the higher the moisture intake rate. As described herein, the surface temperature is based on the ambient environmental conditions surrounding a composite structure. For example, a higher ambient temperature, a higher solar load (a measured amount of sun light exposure on the composite structure), a lower wind speed, and a lower rainfall amount all facilitate increasing the surface temperature of a composite structure. Conversely, a lower ambient temperature, a lower solar load, a higher wind speed, and a higher rainfall amount all facilitate decreasing the surface temperature of a composite structure.

Given the environmental parameter data within parameter profiles 114, module 124 performs a spline interpolation to generate a prediction of what the surface temperature of a composite structure would be if it were exposed to the environmental parameters outlined in parameter profiles 114. A spline interpolation is computer code or a module to generate a cubic curve fit for a surface temperature profile as function of environmental parameters. More specifically, for a given input environmental parameter at an hourly increment, module 124 calculates, via interpolation, the hourly composite structure surface temperature profile 126 over a predetermined period based on the environmental parameter data. Furthermore, allowable moisture content determination system 100 further includes a relative humidity module 128 that generates a relative humidity profile 130 for the plurality of airports. In the exemplary implementation, module 128 calculates, using relative humidity profile 130 and surface temperature profile 126, the relative humidity of the composite structure surface.

In the exemplary implementation, allowable moisture content determination system 100 also includes a fleet utilization profile 132 that includes aircraft operating data. More specifically, fleet utilization profile 132 includes (grounded) non-operating data 134 and (in-flight) operating data 136. Non-operating data 134 includes the time an aircraft spends on the ground, while operating data 136 includes the time the aircraft spends in flight. When an aircraft is in flight, the moisture intake rate of a composite skin is significantly lower than the moisture intake rate of a composite when the aircraft is grounded. Additionally, the surface temperature of a composite can be higher when the aircraft is grounded as compared to the aircraft is in flight. Moisture diffusion rate is typically faster at higher temperature and slower at lower temperature. In flight, the aircraft is traveling at a high altitude where both ambient relative humidity and ambient temperature are very low, below freezing in the case of temperature. As such, moisture absorption is typically very slow or stopped during flight.

However, when the aircraft is grounded, both the moisture intake rate and the surface temperature generally increase depending on a number of factors. More specifically, some of the factors include the same environmental factors described above including ambient temperature, solar load, wind speed, and rainfall. Non-operating data 134 takes into consideration these environmental factors, but also non-environmental factors such as, but not limited to, where the aircraft is stored and the occurrence of routine maintenance checks 138 that may keep the aircraft grounded for an extended period of time. Regarding the storage of the aircraft, when the aircraft is stored in a hangar or in a shaded area, the composite structure surface temperature is typically the same as ambient temperature therefore there is no drying effect taken into account as there is when the aircraft is parked on the open tarmac and exposed directly to high solar load (higher surface temperature than ambient temperature). In such cases when the aircraft is stored, moisture intake for composite surface is higher. Regarding maintenance checks 138, certain components of the aircraft, such as the engine, require servicing or inspection upon reaching various operating milestones, such as operating duration. Some types of maintenance checks are longer in duration than others, however, every maintenance check increases the non-operating time data.

In the exemplary implementation, non-operating data 134 and operating data 136 are representative of average time data of aircraft traveling through the same airports with the highest moisture levels as represented by the environmental parameter data in database 102. Alternatively, non-operating data 134 and operating data 136 are representative of average time data of aircraft traveling through any airport. As such, in the exemplary implementation, each airport includes its own fleet utilization profile 132 that represents non-operating data 134 and operating data 136 for that respective airport.

In the exemplary implementation, allowable moisture content determination system 100 also includes an environmental definition profile 140 for each airport of the plurality of airports. Each environmental definition profile 140 is based on environmental parameter data from database 102, surface temperature profile 126, relative humidity profile 130, and a fleet utilization profile 132. As such, each environmental definition profile 140 includes the environmental data required to calculate an allowable moisture content of a composite structure. In the exemplary implementation, each environmental definition profile 140 is combined with predetermined composite structure data stored in a composite structure database 142. An allowable moisture content determination module 144 performs a moisture analysis to determine an allowable moisture content 146 of a composite structure for each airport based on the information in the environmental definition profiles 140 and database 142. Database 142 includes data related to a plurality of different types of composite structures. For example, for a user-determined composite structure type, database includes a plurality of parameters related to the specified composite structure type that are independent of environmental parameters.

In operation of allowable moisture content determination module 144, a user selects the environmental profile corresponding to the desired airport. The user then selects the type of composite structure to be analyzed and a desired thickness of the composite structure. Once the selections are input into module 144, module 144 calculates an allowable moisture content 146 for the specified composite material based on the selected thickness and the airport environmental definition profile 140. The user may then execute module 144 again using the same environmental definition profile 140 and same composite structure, but with a different thickness. Module 144 then generates a different allowable moisture content 146 based on the newly entered thickness. In one implementation module 144 is instructed to determine the allowable moisture content 146 for each airport over a range of thicknesses, for example between 0.0 inches and 0.8 inches. As a result, the relationship between composite structure thickness and its associated allowable moisture content can be seen.

In order to determine an average allowable moisture content 148 based on a plurality of airports as opposed to a single airport, allowable moisture content module 144 interpolates each of the determined allowable moisture contents 144 of each airport. As a result, module generates a plot 200 (shown in FIG. 2) that illustrates the relationship between composite structure thickness and average allowable moisture content.

Figure 2:
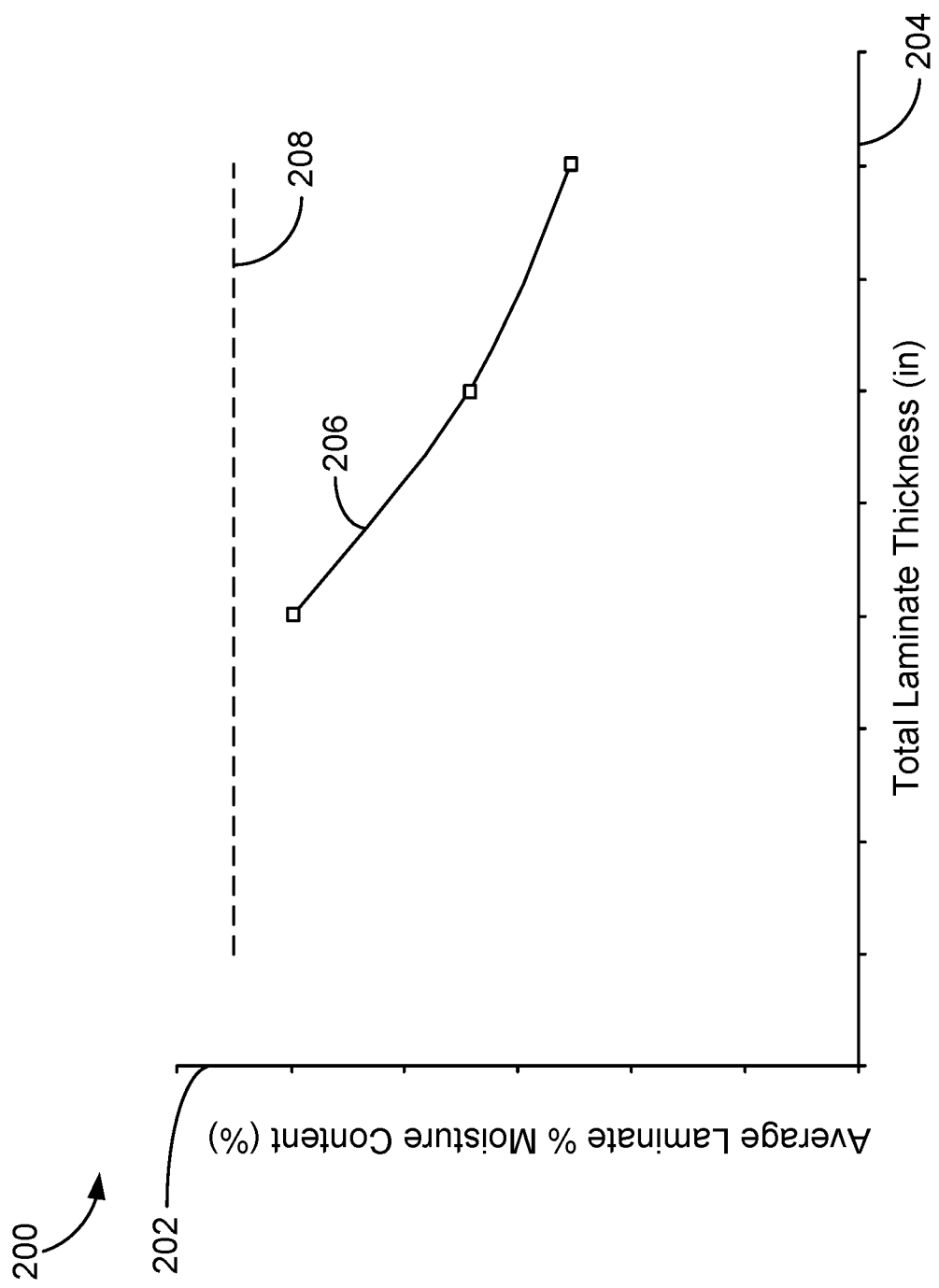
FIG. 2 illustrates an exemplary plot of a determined allowable moisture content of an exemplary composite structure.

Referring now to FIG. 2, plot 200 includes a y-axis of average allowable moisture content shown in percent by weight of the composite structure in its moisture-free state. Plot 200 also includes an x-axis of total composite structure thickness in inches. The relationship between composite structure thickness and average allowable moisture content is shown by segment 206 in plot 200. As illustrated, segment 206 is a non-linear curve that includes a generally negatively-sloped best fit line. As such, segment 206 illustrates that as the thickness of the composite structure increases, the average allowable moisture content percentage decreases. It is known that composite strength is typically higher if its absorbed percentage moisture content is lower. The established percentage moisture content indicates that, for thicker composite structures, it is structurally sound to use lower moisture content (non-saturated level) in lieu of its saturated level, hence this provides better margin of safety or slightly reduce its thickness to increase its margin. That is, because of the non-linear relationship between thickness and moisture content, the thicker a composite structure, the greater amount of moisture per ply it can absorb relative to a thinner composite structure and still maintain an acceptable strength.

Also shown in plot 200 is a dashed line 208 illustrating an example constant average allowable moisture content that does not depend on the composite thickness. This is typically a saturated level of certain composite materials. While composite structures with smaller thicknesses along segment 206 are near line 208, composite structures with larger thicknesses on segment 206 diverge from line 208 and have a significantly lower moisture content as compared to constant line 208. Because the average moisture intake into the composite structure is reduced for thicker gauge structures, the associate strength of the structure increases relative to the thickness, meaning that a thinner gauge composite material will still have an allowable thickness and also be more cost and weight efficient.

Figure 3:
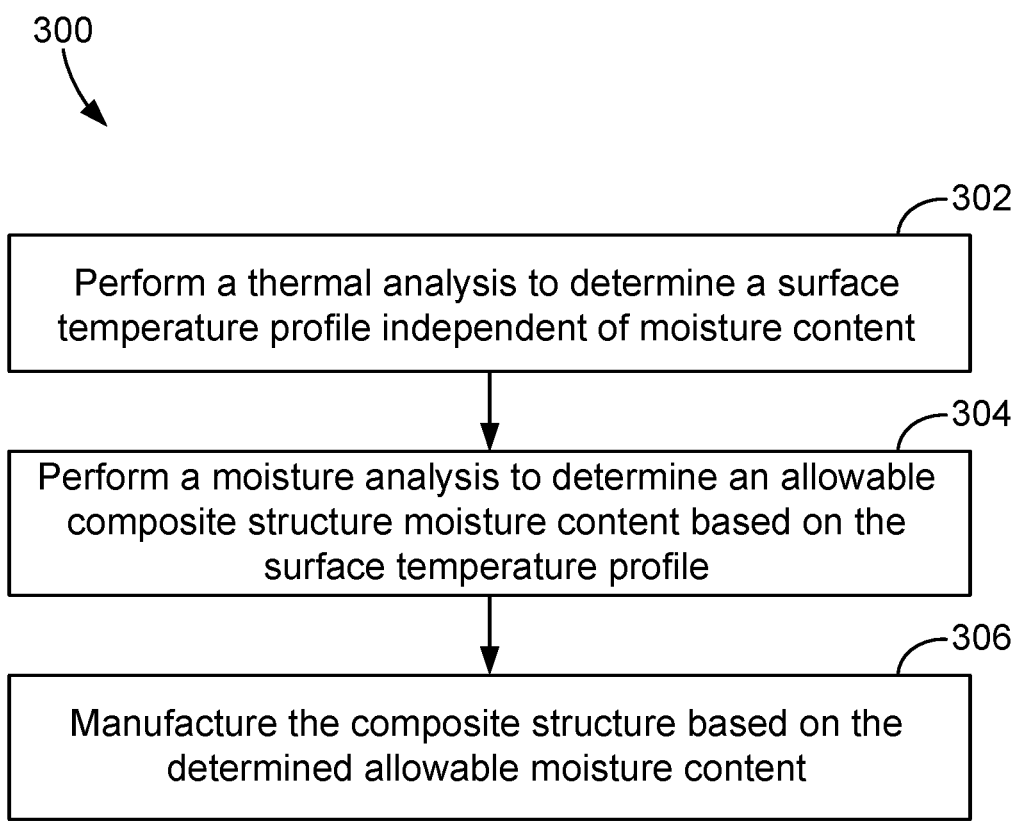
FIG. 3 illustrates an exemplary flow diagram of a method for determining an allowable moisture content of a composite structure.

FIG. 3 illustrates an exemplary method 300 of determining an allowable moisture content of a composite structure. Method 300 includes performing 302 a thermal analysis on the composite structure to determine a surface temperature profile 126 (shown in FIG. 1) of the composite structure such that surface temperature profile 126 is independent of a moisture content of the composite structure. In the exemplary implementation, the thermal analysis is performed primarily by surface temperature module 124 (shown in FIG. 1) to determine surface temperature profile 126 of a composite structure that is exposed to the environmental parameters stored in database 102 (shown in FIG. 1). Method 300 also includes performing 304 a moisture analysis on the composite structure to determine an allowable moisture content 148 (shown in FIG. 1) of the composite structure. The moisture analysis is carried out by allowable moisture content determination module 144 (shown in FIG. 1) and is based, at least in part, on surface temperature profile 126. Method 300 also includes manufacturing 306 the composite structure having a thickness based on the determined allowable moisture content.

In the exemplary implementation, the thermal analysis step is de-coupled from the moisture analysis step such that the thermal analysis, and therefore, the surface temperature profile, is determined independent of a moisture content of the composite structure. More specifically, the thermal analysis is calculated iteratively over a first time period (e.g. hourly), and the moisture analysis is calculated iteratively over a second time period, monthly or yearly, that is longer than the first time period. Determining the thermal analysis independently of the moisture analysis enables the calculations to be performed in a shorter amount of time and with less computer power than conventional methods where the thermal analysis and moisture analysis are performed simultaneously.

Figure 4:
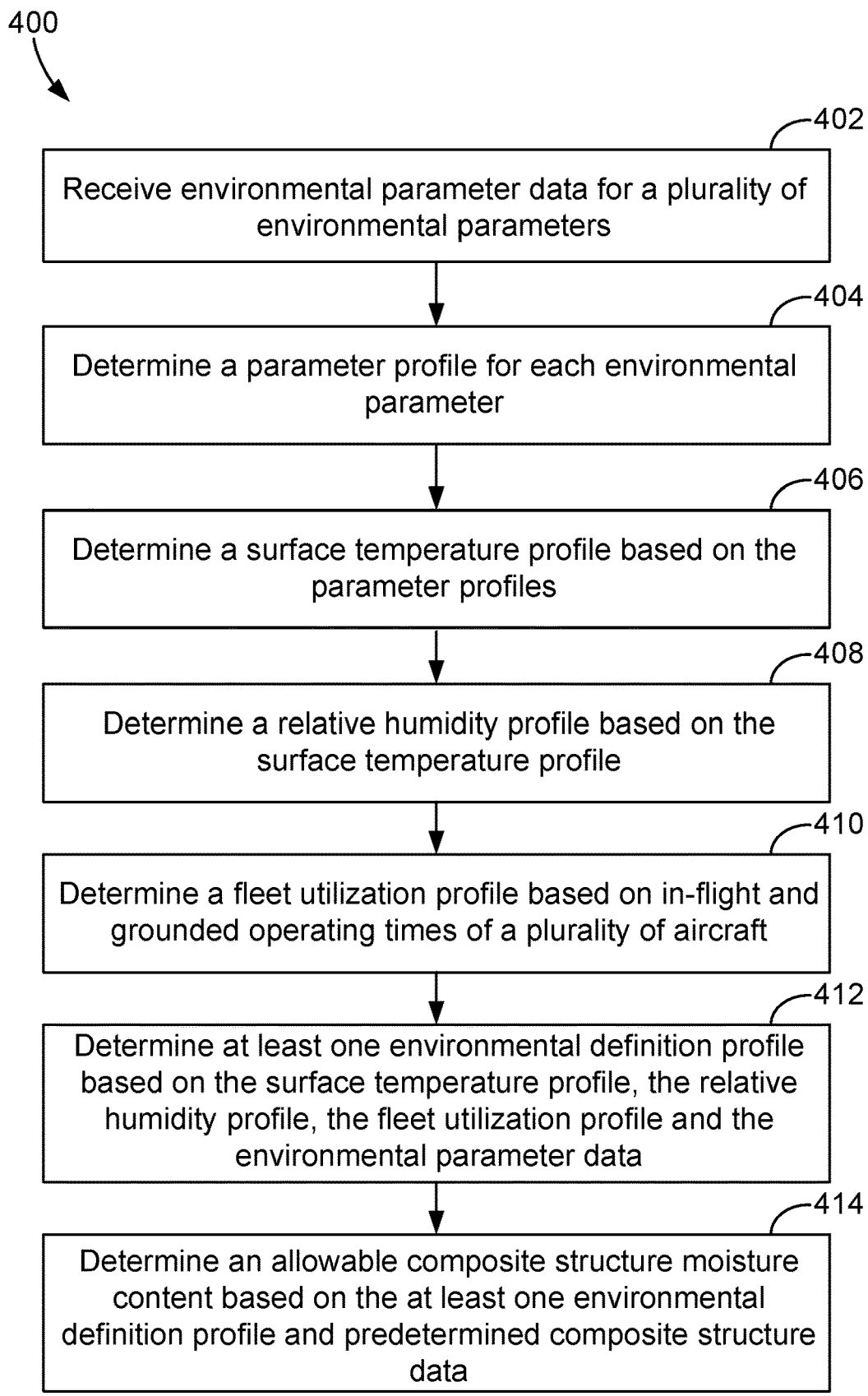
FIG. 4 illustrates an exemplary flow diagram of another method for determining an allowable moisture content of a composite structure.

FIG. 4 illustrates another method 400 of determining an allowable moisture content of a composite structure. Method 400 includes receiving 402, by a database, such as database 102 (shown in FIG. 1), environmental parameter data for a plurality of environmental parameters. As described herein, the environmental parameter data is collected from a plurality of airports over a predetermined period of time. Method 400 also includes determining 404, by a parameter profile module such as module 112 (shown in FIG. 1), a parameter profile such as parameter profile 114 (shown in FIG. 1), for each environmental parameter having data stored in the database. The environmental parameter data is input into the parameter profile module to determine the associated parameter profile. A surface temperature profile such as profile 126 (shown in FIG. 1) is then determined 406 using a surface temperature module such as module 124 (shown in FIG. 1) based on the parameter profiles. More specifically, the parameter profiles are input into the surface temperature module to generate the surface temperature profile. The determined surface temperature profile is then used, by a relative humidity module such as module 128 (shown in FIG. 1), to determine 408 a relative humidity profile such as profile 130 (shown in FIG. 1).

Method 400 also includes determining 410 a fleet utilization profile such as profile 132 (shown in FIG. 1) based on in-flight operating data such as data 136 (shown in FIG. 1) and grounded non-operating data such as data 134 (shown in FIG. 1). The flight utilization profile, the surface temperature profile, the relative humidity profile, and the environmental parameter data are then combined to determine 412 an environmental definition profile such as profile 140 (shown in FIG. 1) for each airport from which the environmental parameter data is collected. Method 400 further includes determining 414, by an allowable moisture content module such as module 144 (shown in FIG. 1), an allowable moisture content of a composite structure based on the environmental definition profiles and predetermined composite structure data input into the moisture content module from a composite structure database such as database 142 (shown in FIG. 1).

Figure 5:
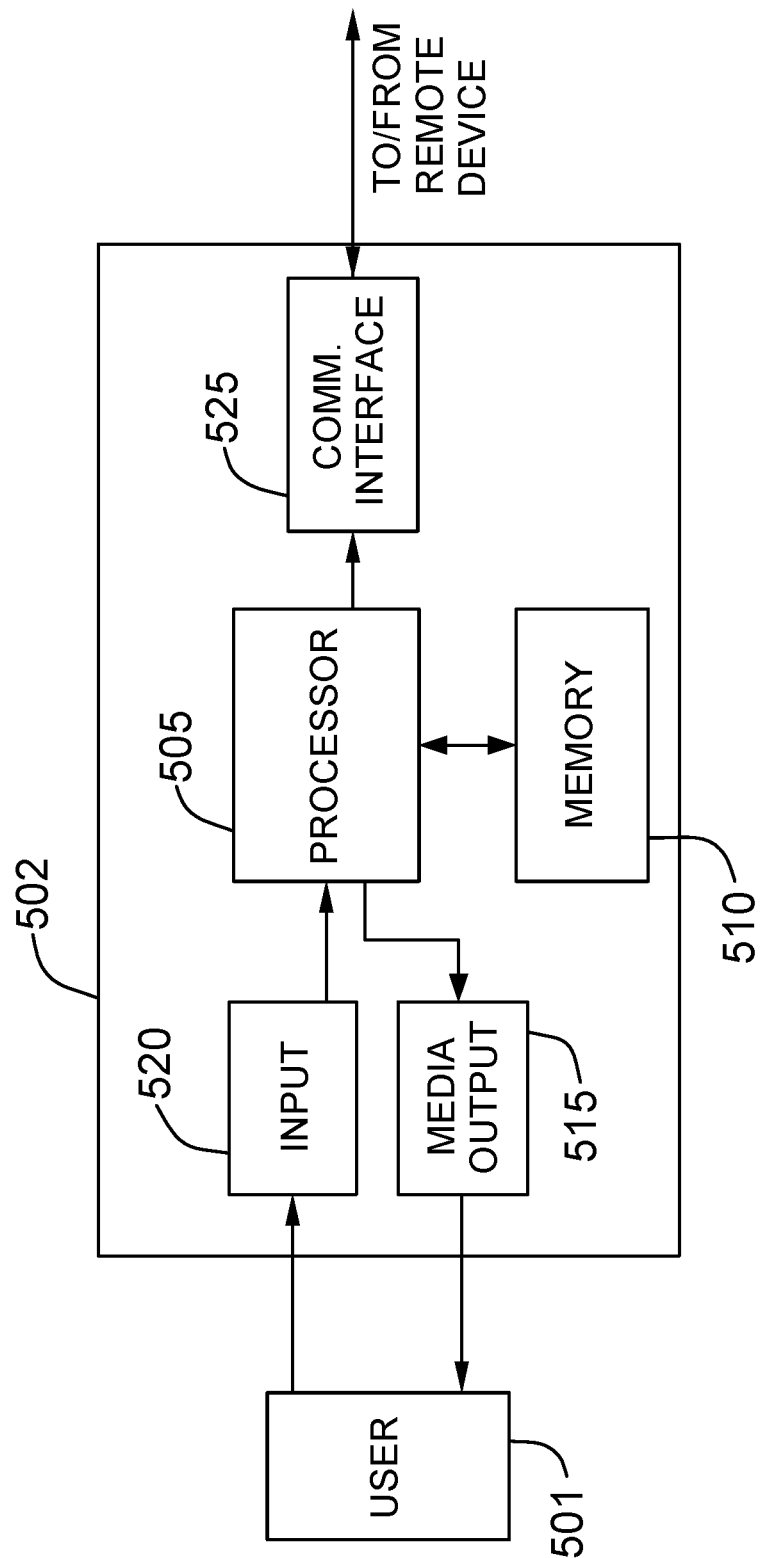
FIG. 5 is a block diagram of an example computing device used in the allowable moisture content determination system of FIG. 1.

FIG. 5 is a block diagram of an example computing device 502 used in the allowable moisture content determination system 100 of FIG. 1. In the exemplary implementation, computing device 502 is capable of executing machine readable instructions to implement the allowable moisture content determination system 100. Computing device 502 includes at least one processor 505 for executing instructions. In some implementations, executable instructions are stored in a memory device 510. Processor 505 may include one or more processing units (e.g., in a multi-core configuration). One or more memory devices 510 are any one or more devices allowing information such as executable instructions and/or other data to be stored and retrieved. One or more memory devices 510 may include one or more computer-readable media.

Computing device 502 also includes at least one media output component 515 for presenting information to a user 501. Media output component 515 is any component capable of conveying information to a user 501. In some implementations, media output component 515 includes an output adapter such as a video adapter and/or an audio adapter. An output adapter is operatively coupled to processor 505 and operatively couplable to an output device such as a display device (e.g., a liquid crystal display (LCD), organic light emitting diode (OLED) display, cathode ray tube (CRT), or "electronic ink" display) or an audio output device (e.g., a speaker or headphones). In at least some implementations, media output component 515 causes one or more of plots 200 to be displayed to user 501.

In some implementations, computing device 502 includes an input device 520 for receiving input from user 501. Input device 520 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 515 and input device 520.

Computing device 502 additionally includes a communication interface 525, which is communicatively couplable to a remote device such as another computing device 502. Communication interface 525 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in one or more memory devices 510 are, for example, computer-readable instructions for providing a user interface to user 501 via media output component 515 and, optionally, receiving and processing input from input device 520. A user interface may include, text, graphics, and/or sound that enable user 501 to interact with computing device 502.

The method and systems outlined herein describe quantifying a conservative but realistic moisture intake for carbon fiber reinforced polymer (CFRP). The method provides a process for accounting for variables that effect moisture intake, specifically environmental exposure (e.g.; solar exposure, ambient temperature, ambient relative humidity, substrate thickness, fleet utilization). The pseudo-coupling analysis of temperature and moisture diffusion method enables conducting long term moisture intake calculations over a time span of 20-40 years with minimal computing resources. The developed method also defines values of moisture intake a function of substrate thickness for a well-defined environmental exposure, duration, fleet utilization and operation. As a result, composite structures are manufactured according to the newly calculated allowable moisture content based on its thickness such that thinner gauge composite structures are produced that maintain a required amount of strength, but reduce the overall weight of the aircraft and reduce the manufacturing costs associated therewith.

Although specific features of various examples of the invention may be shown in some drawings and not in others, this is for convenience only. In accordance with the principles of the invention, any feature of a drawing may be referenced and/or claimed in combination with any feature of any other drawing.

This written description uses examples to disclose various examples, which include the best mode, to enable any person skilled in the art to practice those examples, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of designing and manufacturing composite structures for use in aircraft, said method comprising:
    performing a thermal analysis on a model composite structure to determine a temporal surface temperature profile of the model composite structure based on temporal environmental parameter profiles associated with at least one location in which the model composite structure is selectively positionable, the temporal environmental parameter profiles determined based on environmental data collected by at least one sensor at the at least one location,
    performing a moisture content analysis on the model composite structure, wherein the moisture content analysis is based on the determined temporal surface temperature profile and a desired thickness of a composite structure to be manufactured, wherein the temporal surface temperature profile is determined independently of the moisture content analysis,
    wherein the thermal analysis is performed iteratively with a first time period and the moisture content analysis is performed iteratively with a second time period that is longer than the first time period;
    determining an allowable moisture content of the model composite structure based on the moisture content analysis;
    determining a number of plies of material within the desired thickness of the composite structure sufficient to maintain the allowable moisture content;
    designing the composite structure based on the determined number of plies of material; and
    manufacturing the composite structure based on the design that includes the number of plies of material.

2. The method according to claim 1, wherein performing a thermal analysis based on temporal environmental parameter profiles comprises receiving environmental parameter data related to a plurality of environmental parameters from an environmental parameter database, the plurality of environmental parameters including temperature, solar load, wind speed, and rainfall, wherein the environmental parameter data is collected from a plurality of airports, in which the model composite structure is selectively positionable, over a predetermined time period.

3. The method according to claim 2, further comprising determining a temporal environmental parameter profile for each environmental parameter of the plurality of environmental parameters.

4. The method according to claim 1, wherein performing the thermal analysis comprises:
monitoring at least one weather parameter that includes temperature, solar load, wind speed, and rainfall at a location in which the model composite structure is selectively positionable; and
determining the temporal surface temperature profile based on the monitored weather parameter.

5. The method according to claim 1, wherein performing the moisture content analysis comprises:
determining a relative humidity at each of a plurality of airports in which the model composite structure is selectively positionable as a component of an aircraft traveling between the plurality of airports; and
wherein performing the moisture content analysis on the model composite structure is based on the determined relative humidity at which the model composite structure is selectively positionable.

6. The method according to claim 1 further comprising:
determining a fleet utilization profile for each airport of a plurality of airports, wherein each fleet utilization profile is based on in-flight operating data and grounded non-operating data for aircraft, formed from at least one composite structure, operating from each airport of the plurality of airports, wherein a temperature difference is defined based on whether the aircraft is in-flight, defined by a first temperature, versus being grounded, defined by a second temperature; and
performing the thermal analysis on the model composite structure associated with the aircraft based on the temperature difference.

7. A system for use in designing composite structures for use in aircraft, the system comprising:
an environmental parameter database comprising environmental parameter data, related to a plurality of environmental parameters, collected by at least one sensor at a plurality of airports;
a computing device comprising a processor configured to:
generate a plurality of temporal environmental parameter profiles based on the environmental parameter data, wherein each environmental parameter profile is based on an environmental parameter of the plurality of environmental parameters,
perform a thermal analysis to generate a temporal surface temperature profile of a model composite structure for the plurality of airports, wherein the temporal surface temperature profile is generated based on the generated temporal environmental parameter profiles;
perform a moisture content analysis based on the generated temporal surface temperature profile and a desired thickness of a composite structure to be manufactured, wherein the surface temperature profile is generated independently of the moisture content analysis;
determine an allowable moisture content of the model composite structure based on the moisture content analysis;
determine a number of plies of material within the desired thickness of the composite structure sufficient to maintain the allowable moisture content; and
design the composite structure based on the determined number of plies of material for obtaining the desired thickness of the composite structure having a moisture content percentage by weight of the composite structure that is less than a fully saturated level, the number of plies determined based on the environmental parameter profiles and on predetermined composite structure data,
wherein the thermal analysis is performed iteratively with a first time period and the moisture content analysis is performed iteratively with a second time period that is longer than the first time period.

8. The system according to claim 7, wherein the processor is further configured to generate the temporal environmental parameter profiles based on at least one of: temperature, solar load, wind speed, and rainfall at a location in which the composite structure is selectively positionable.

9. The system according to claim 7, wherein the processor is further configured to generate the temporal environmental parameter profiles further based on an ambient relative humidity at the plurality of airports in which the composite structure is selectively positionable.

10. The system according to claim 7, wherein the processor is further configured to generate the temporal environmental parameter profiles based on in-flight operating data and grounded non-operating data for aircraft, formed from at least one composite structure, operating from each airport of the plurality of airports, wherein a temperature difference is defined based on whether the aircraft associated with the model composite structure is in-flight, defined by a first temperature, versus being grounded, defined by a second temperature.

11. The system according to claim 10, further comprising a composite structure database configured to store data related to the model composite structure, wherein the processor is further configured to determine the moisture content of the model composite structure based on the composite structure data.

12. At least one non-transitory computer-readable storage media having computer-executable instructions embodied thereon, wherein when executed by at least one processor, the computer-executable instructions cause the at least one processor to:
generate a plurality of temporal environmental parameter profiles based on environmental parameter data collected by at least one sensor at a plurality of airports, wherein each environmental parameter profile is based on an environmental parameter of the plurality of environmental parameters;
perform a thermal analysis on a model composite structure to determine a temporal surface temperature profile of the model composite structure for the plurality of airports, wherein the temporal surface temperature profile is generated based on the generated temporal environmental parameter profiles; and
perform a moisture content analysis on the model composite structure to determine a moisture content of the model composite structure, wherein the moisture content analysis is based on the determined temporal surface temperature profile and a desired thickness of a composite structure to be manufactured, wherein the surface temperature profile is determined independently of the moisture content analysis; and
determine an allowable moisture content of the model composite structure based on the moisture content analysis;
determine a number of plies of material within the desired thickness of the composite structure sufficient to maintain the allowable moisture content; and designing the composite structure based on the determined number of plies of material for obtaining the desired thickness of the composite structure having a moisture content percentage by weight of the composite structure that is less than a fully saturated level, the number of plies determined based on the environmental parameter profiles and on predetermined composite structure data, wherein the thermal analysis is performed iteratively with a first time period and the moisture content analysis is performed iteratively with a second time period that is longer than the first time period.

13. The non-transitory computer-readable storage media according to claim 12, wherein the computer-executable instructions further cause the at least one processor to receive environmental parameter data related to a plurality of environmental parameters from an environmental parameter database, the environmental parameter data including temperature, solar load, wind speed, and rainfall, wherein the environmental parameter data is collected from a plurality of airports, in which the composite structure is selectively positionable, over a predetermined time period.

14. The non-transitory computer-readable storage media according to claim 12, wherein the computer-executable instructions further cause the at least one processor to determine a fleet utilization profile for each airport of a plurality of airports, wherein each fleet utilization profile is based on in-flight operating data and grounded non-operating data for aircraft operating from each airport of the plurality of airports, wherein a temperature difference is defined based on whether the aircraft associated with the composite structure is in-flight, defined by a first temperature, versus being grounded, defined by a second temperature.

15. The non-transitory computer-readable storage media according to claim 14, wherein the computer-executable instructions further cause the at least one processor to:

receive, from a composite structure database, data related to the composite structure; and determine the moisture content of the composite structure based on the composite structure data.

* * * * *